United States Patent [19]
Yoshioka et al.

[11] Patent Number: 5,869,300
[45] Date of Patent: Feb. 9, 1999

[54] METHOD FOR PRODUCING L-GLUTAMIC ACID BY CONTINUOUS FERMENTATION

[75] Inventors: Tatsuya Yoshioka; Toshimasa Ishii; Yoshio Kawahara; Yosuke Koyama; Eiko Shimizu, all of Kawasaki, Japan

[73] Assignee: Ajinomoto Co., Inc., Tokyo, Japan

[21] Appl. No.: 974,919

[22] Filed: Nov. 20, 1997

[30] Foreign Application Priority Data

Nov. 21, 1996 [JP] Japan ................................. 8-310845

[51] Int. Cl.⁶ .............................. C12P 13/14; C12P 13/18
[52] U.S. Cl. ........................ 435/110; 435/111; 435/813; 435/840; 435/843
[58] Field of Search ................................ 435/111, 110, 435/840, 843, 813

[56] References Cited

U.S. PATENT DOCUMENTS 5,492,818  2/1996  Nakazawa et al. ..................... 435/111

*Primary Examiner*—Herbert J. Lilling
*Attorney, Agent, or Firm*—Oblon, Spivak, McClelland, Maier & Neustadt, P.C.

[57] ABSTRACT

A method for producing L-glutamic acid, comprising inoculating a microorganism having an ability to produce L-glutamic acid, in a liquid medium containing a carbon source and a nitrogen source, conducting continuous L-glutamic acid fermentation in which both a carbon source and a nutrient having an effect of promoting bacterial growth are fed so as to make the microorganism grow, and then collecting L-glutamic acid produced and accumulated in a culture broth.

12 Claims, 5 Drawing Sheets

METHOD FOR PRODUCING L-GLUTAMIC ACID BY CONTINUOUS FERMENTATION

BACKGROUND OF THE INVENTION

The present invention relates to a method for efficiently producing L-glutamic acid by a continuous fermentation method. L-Glutamic acid is widely utilized as a food material such as seasoning and a raw material of various chemical products.

Following the increase of the demand for L-glutamic acid in recent years, the development of an industrially advantageous production method thereof has been desired, and the production methods thereof as described below have been invented.

(1) Batch culture method, Fed-batch culture method

Compared with the continuous culture method, these culture methods are advantageous in that the equipment therefor is simple and the cultivation is terminated for a short period and that damage due to contaminated bacteria is less. However, the concentration of L-glutamic acid in the culture broth is increased over time, and the productivity and yield thereof are decreased under the influence of osmotic pressure or inhibition due to the products. Thus, it is difficult to maintain stably high yield and high productivity for a long time.

(2) Continuous culture method

The continuous culture method is characteristic in that a high yield and a high productivity can be retained for a long time, by avoiding the accumulation of an objective product at a high concentration in a fermentor.

The most simple and general mode of continuous culture method is a single-fermentor continuous culture method, and a great number of reports on the single-fermentor continuous culture method applied for amino acid fermentation, including L-lysine fermentation and L-arginine fermentation, have been issued (Lys: Toshihiko Hirao et. al., Appl. Microbiol. Biotechnol., 32, 269–273 (1989), Arg: Tomoki Azuma et. al., J. Ferment. Technol., 66 (3), 285–290 (1988)). During such fermentation of L-lysine and L-arginine, generally, the bacterial growth and the production of the objective amino acids simultaneously occur, and therefore, the single-fermentor continuous culture method has been readily applicable to these fermentation.

On the other hand, it has been considered that the application of the single-fermentor continuous culture method to L-glutamic acid fermentation is difficult. In other words, conventionally, it has been considered that L-glutamic acid cannot be accumulated at a higher level by such L-glutamic acid fermentation, unless the bacterial growth is terminated by any method including limitation of biotin which is an essential factor for the bacterial growth, addition of antibiotics such as penicillin, addition of surfactants and temperature change (1. Japanese Journal of Fermentation Engineering Association, Vol. 41, No. 12, 645–651 (1963)); 2. Recent Japanese Industrial Chemistry, Vol. 23, 121–142, Asakura Shoten). So as to produce a greater amount of L-glutamic acid by the batch culture method and the fed-batch culture method, the culture conditions should be set to terminate the bacterial growth. Thus, it has been considered that the fermentation of L-glutamic acid by the continuous culture method is unsuitable because the bacteria simply wash out under conventional culture conditions to terminate the bacterial growth, so that the bacteria cannot be maintained in the fermentor. As to research works of the continuous culture method for L-glutamic acid fermentation, hence, research works of multiple-fermentor continuous culture method comprising promoting the bacterial growth in a first fermentor and suppressing the bacterial growth in a second fermentor to produce L-glutamic acid, have been carried out at the early stage, such as those by Mr. Ueda, et. al. (Japanese Journal of Fermentation Engineering Association, Vol. 41, No. 9, 450–458, 1964) and Mr. Mimura, et. al. (Japanese Journal of Fermentation Engineering Association, Vol. 42, No. 2, 70–78, 1964).

Subsequently, two methods, namely a cell recycle culture method and an immobilized bacteria culture method, have been developed, as culture methods based on the concept that a process of bacterial growth and a process of producing L-glutamic acid should be independently carried out.

Firstly, the cell recycle culture method is a method comprising extracting the culture broth where L-glutamic acid is accumulated but the bacterial growth is terminated and separating L-glutamic acid from the bacteria to recycle only the bacteria (Unexamined Published Japanese Patent Application No. 52-136985; Unexamined Published Japanese Patent Application No. 60-133891 or Unexamined Published Japanese Patent Application No. 62-48394), and the method can maintain a high yield and a high productivity for a relatively long time. However, the method requires a system to separate the bacteria from the cultured broth, disadvantageously, so that the cultivation system is complex. Furthermore, because the bacteria terminating bacterial growth are recycled by the cell recycle culture method, the ability of the bacteria of themselves to produce L-glutamic acid is decreased over time, which limits the cultivation time.

Although the immobilized bacteria culture method can also recover L-glutamic acid at a high yield and a high productivity (H. S. KIM et. al., Biotechnology and Bioengineering, Vol. 26, 2167–2174 (1982)), on contrast, a carrier to immobilize the bacteria is expensive from the respect of practical application for the production of L-glutamic acid and additionally, the method has a great number of problems to be overcome, such as carrier exchange technique. Therefore, the method is not essentially suitable for industrial applications.

As has been described above, the culture conditions to produce L-glutamic acid at a high yield by the batch culture method and the fed-batch culture method require complete termination of the bacterial growth, and therefore, the ability of a bacterium to produce L-glutamic acid is decreased at the latter stage of culture, which causes difficulty in improving the productivity. By the conventional continuous culture method, additionally, a system is required to further add bacteria to a fermentor or to recycle the bacteria, and therefore, the method has many problems so as to attain industrial application as follows: the whole system is complex and the possibility of bacterial contamination is increased and that the high productivity can be retained with much difficulty because of cultivation under conditions to terminate the bacterial growth.

So as to meet the enlargement of the need toward L-glutamic acid and produce L-glutamic acid at a lower cost, the productivity of L-glutamic acid fermentation should be elevated at a higher level than conventional ones.

SUMMARY OF THE INVENTION

A problem that the present invention solves is to develop a continuous culture method for L-glutamic acid fermentation at a high productivity in a simple system, comprising simultaneously promoting bacterial growth and L-glutamic acid production in a fermentor.

The present inventors have made investigations to modify the production method of L-glutamic acid by conventional fermentation process, and consequently, the inventors have found that by inoculating a microorganism having the ability to produce L-glutamic acid which belongs to the genus Brevibacterium or Corynebacterium, in a liquid medium containing a carbon source and a nitrogen source, and continuing the cultivation under the feeding of both a carbon source and a nutrient having the effect of promoting the bacterial growth, L-glutamic acid is produced at a high productivity and a high yield during continuous culture, while controlling the bacterial growth through temperature, surfactants, antibiotics, biotin concentration and the like, with no termination of the bacterial growth. In other words, the inventors have achieved the present invention based on the finding that L-glutamic acid is efficiently produced while growing a fresh cell with a higher productivity, not under conventional conditions to terminate the bacterial growth; that the bacterial cell weight in the fermentor can be maintained owing to the growth of bacteria even after the culture broth is extracted, so that high productivity can be retained throughout continuous culture for a long time.

In an aspect of the present invention, it is provided a method for producing L-glutamic acid, comprising inoculating a microorganism having an ability to produce L-glutamic acid, in a liquid medium containing a carbon source and a nitrogen source, conducting continuous L-glutamic acid fermentation in which both a carbon source and a nutrient having an effect of promoting bacterial growth are fed so as to make the microorganism grow, and then collecting L-glutamic acid produced and accumulated in a culture broth.

The microorganism is preferably a microorganism having a property to produce L-glutamic acid when the microorganism is cultured in a liquid medium at a biotin concentration of 10 μg/liter or more with no addition of any substance suppressing a biotin action.

DETAILED DESCRIPTION OF THE INVENTION

Figure 1:
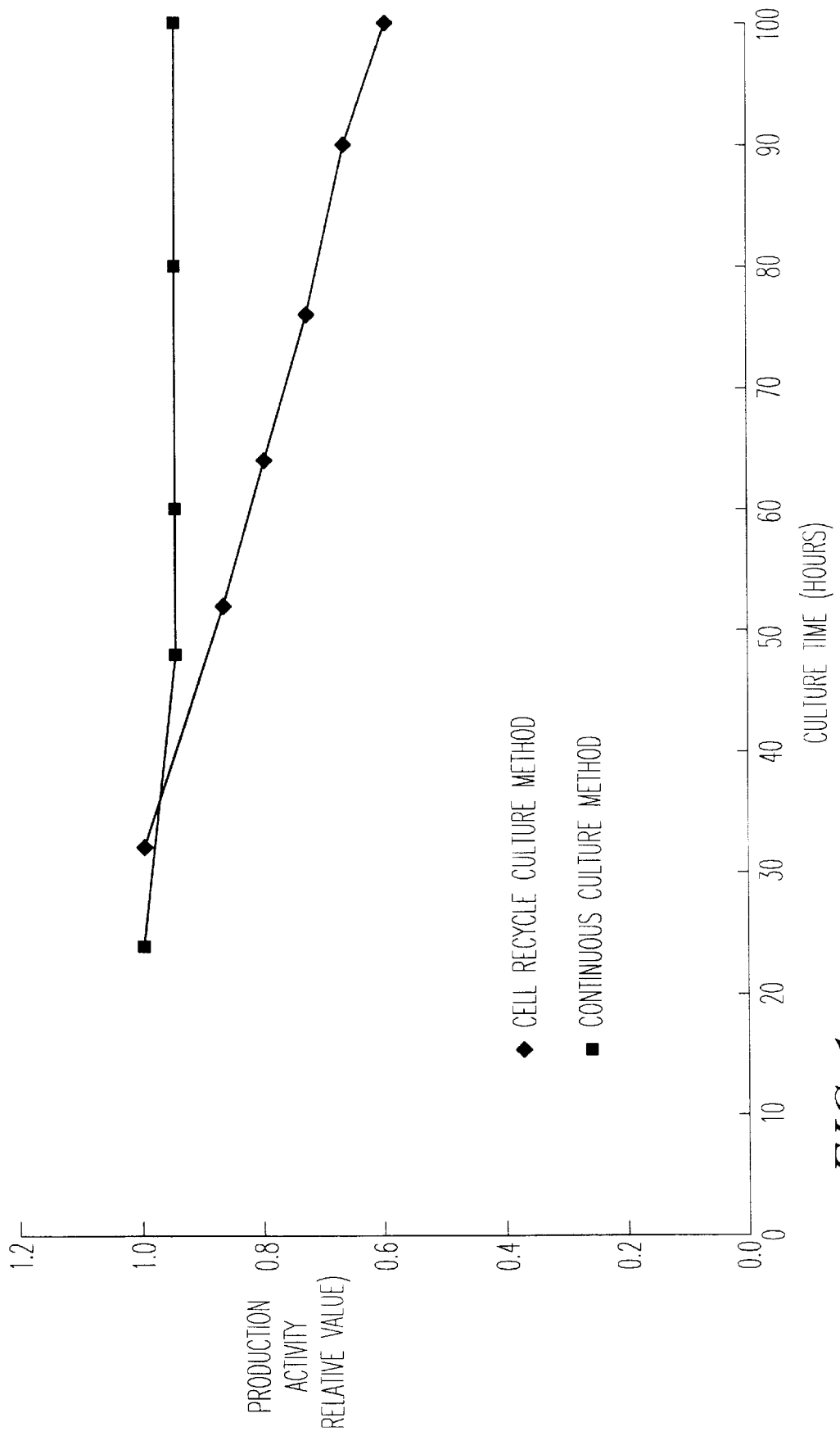
FIG. 1 shows change of activity of producing L-glutamic acid throughout the cultivation by the present culture method and the cell recycle culture method.

In accordance with the present invention, any microorganism having the ability to accumulate L-glutamic acid is used, with no specific limitation. For example, the following bacterial strains may be included.
Brevibacterium lactofermentum ATCC 13869
Brevibacterium lactofermentum FERM BP-4172 (AJ 12821)
Brevibacterium lactofermentum FERM BP-1363 (AJ 12300)
Brevibacterium lactofermentum FERM BP-5189 (AJ 13029)
Brevibacterium flavum ATCC 14067
Brevibacterium flavum FERM BP-4173 (AJ 12822)
Brevibacterium divaricatum ATCC 14020
Brevibacterium saccharolyticum ATCC 14066
Corynebacterium glutamicum ATCC 13032
Corynebacterium glutamicum FERM BP-4174 (AJ 12823)
Corynebacterium acetoacidophilum ATCC 13870

It has been well known generally that among bacteria accumulating L-glutamic acid, some bacteria accumulate L-glutamic acid in a culture medium containing excess amounts of biotin in the presence of a substance suppressing the action of biotin, while some bacterial strains among the bacteria accumulate L-glutamic acid in the absence of a substance suppressing the action of biotin. Among them, bacteria accumulating L-glutamic acid in the absence of a substance suppressing the action of biotin are preferable microorganisms in accordance with the present invention. More specifically, in accordance with the present invention, the microorganism having the ability to accumulate L-glutamic acid is preferably a microorganism having the property to produce and accumulate L-glutamic acid when cultured in a liquid medium containing biotin at a concentration of 10 μg/liter or more, for example 10 to 1000 μg/l with no addition of any substance suppressing the action of biotin.

Furthermore, if a bacterial strain having a property of producing and accumulating L-glutamic acid such as mutant strains having a reduced α-ketoglutarate dehydrogenase activity and the ability to produce L-glutamic acid, when cultured in a liquid medium of a biotin concentration of 10 μg/l or more, for example 10 to 1000 μg/l, like FERM BP-4172 (AJ 12821), FERM BP-4173 (AJ 12822), and FERM BP-4174 (AJ 12823) (Unexamined Published Japanese Patent Application No. 6-237779) is used, the bacterial strain does not require addition of a substance suppressing the action of biotin, such as surfactants and antibiotics, whereby culture control for L-glutamic acid fermentation can be done readily for a long time and L-glutamic acid can be produced inexpensively from the respect of cost. Furthermore, the same is true with a mutant strain having mutation of temperature sensitivity to substances suppressing the action of biotin and having the ability to accumulate L-glutamic acid in a culture medium containing excess biotin in the absence of any substance suppressing the action of biotin, such as FERM BP-5189 (AJ 13029) (International Publication No. WO 96/06180).

As the medium to be used in accordance with the present invention, routine liquid media appropriately containing a carbon source, a nitrogen source, inorganic salts, and organic micronutrients such as amino acid and vitamin, are satisfactory. As the carbon source, sugars such as glucose, sucrose, fructose, galactose and lactose; saccharified starch solutions containing these sugars; sweet potato molasses, sugar beet molasses, and cane molasses; and additionally, organic acids such as acetic acid, alcohols such as ethanol and glycerin and the like, may be used. As the nitrogen source, ammonia gas, aqueous ammonia, ammonium salts, urea, nitrates, organic nitrogen sources for supplementary use, for example oil cake, soybean protein hydrolysis solution (hydrolysate), casein degradation products, other amino acids, corn steep liquor, yeast extract, meat extracts, and peptides such as peptone, extracts of various bacteria used for fermentation and hydrolysis products thereof may be added. As the inorganic salts, phosphates, magnesium salts, calcium salts, iron salts, manganese salts and the like may be appropriately added.

When a microorganism to be used in accordance with the present invention requires a specific nutrient for its growth, the nutrient is added as a preparation or a natural product containing the same. Additionally, defoaming agents may be used if necessary.

In accordance with the present invention, preferably, the concentration of the carbon source in the culture medium is maintained at 5 g/liter or less. The reason is that the loss of sugar contents due to the extraction of the culture broth is kept at minimum.

The cultivation of the microorganism is generally carried out under aerobic conditions within a range of pH 5 to 8 and a temperature range of 25° to 40° C. The pH of the culture broth is adjusted to a determined value within the range, by using inorganic or organic acids and alkaline substances and additionally urea, calcium carbonate and ammonia gas. If the oxygen feeding rate should be elevated, means such as the addition of oxygen into air to keep the oxygen concentration at 21% or more; culturing under pressure or the elevation of agitation speed; and the elevation of aeration rate may be used.

If continuous culture of a bacterial strain advantageously accumulating L-glutamic acid in the presence of a substance suppressing the action of biotin is carried out, by controlling and maintaining the bacterial growth at some extent at an appropriate temperature (25° to 40° C.), an appropriate surfactant concentration (polyoxyethylene sorbitan monopalmitate; 100 to 5000 mg/liter), an appropriate concentration of antibiotics (penicillin; 0.1 to 50 U/ml), and an appropriate biotin concentration (5 to 5000 $\mu$g/liter), L-glutamic acid is produced at a higher yield and at a high productivity, together with the bacterial growth.

In the case of Brevibacterium lactofermentum ATCC 13869, for example, if the control and maintenance of the bacterial growth is conducted with polyoxyethylene sorbitan monopalmitate, the concentration thereof is preferably at a concentration of 100 to 1000 mg/liter.

So as to efficiently accumulate L-glutamic acid, biotin or a derivative thereof can be added to the culture medium, if necessary. Additionally, a fatty acid or an ester thereof, or penicillin or a derivative thereof may be added advantageously. The addition of biotin or a derivative thereof is effective for helping a bacterium retain the ability to produce L-glutamic acid for a long time. The amount thereof to be added is satisfactorily adjusted to a final concentration in the culture broth of about 5 to 5000 $\mu$g/liter. As the fatty acid, a saturated higher fatty acid of 12 to 18 carbon atoms is preferable; the ester thereof is selected from glycerol ester, sorbitan ester, sucrose ester, polyethylene glycol ester, and polyoxyethylene sorbitan ester. When a fatty acid or an ester thereof and penicillin or a derivative thereof are to be added, they are added to final concentrations below normal concentrations thereof, namely concentrations such that the growth can be maintained with no cessation of the growth. For example, when the fatty acid or the ester thereof is added, the concentration thereof is appropriately at about 100 to 1000 mg/liter; when the penicillin or the derivative thereof is added, the concentration thereof in a medium is appropriately at about 0.2 to 10 U/ml.

In the continuous L-glutamic acid fermentation, both a carbon source and a nutrient having an effect of promoting bacterial growth (growth promoting nutrient) are fed. Examples of the carbon source include those mentioned in the above. The growth promoting nutrient is not specifically restricted provided that the nutrient promotes bacterial growth. The term "bacterial growth" refer to an increase in a number of cells. Examples of the growth promoting nutrient include a nitrogen source, inorganic salts, and organic micronutrients such as amino acid and vitamin.

The carbon source and the growth promoting nutrient are fed in amounts effective to keep both of bacterial growth and L-glutamic acid production. The carbon source and the growth promoting nutrient are preferably fed in forms of solution. A solution containing the both or solutions separately containing them may be fed as a feeding solution or solutions.

Batch culture or fed-batch culture may satisfactorily be done at the initial stage of continuous culture in accordance with the present invention, to increase the concentration of L-glutamic acid and the bacterial cell concentration, and thereafter, continuous culture (and extraction) may be initiated; or the bacteria at a high concentration may be inoculated and continuous culture may be carried out once the cultivation is initiated.

Supply of the feeding solution and extraction should be started from an appropriate stage. The timing of the supply of the feeding solution is not necessarily adjusted to the timing of extraction. Supply of the feeding solution and extraction may satisfactorily be carried out continuously or intermittently. To the feeding solution are added nutrients required for the bacterial growth as described above, so as to promote continuous bacterial growth.

The productivity is calculated by the following formula:

$$\text{Productivity (g/l/hr)} = \frac{\text{Glutamic acid concentration in drawn-out solution (extract solution) (g/l)} \times \text{Flow rate of the drawn-out solution (l/hr)}}{\text{Working volume in a fermentor (l)}}$$

According to the method of the present invention, the productivity of L-glutamic acid is increased by about 2-fold the productivity by the fed-batch culture method (40-hour culture time).

Compared with the cell recycle culture method, apparently, the activity of producing L-glutamic acid can be maintained for a long time, advantageously, by the present culture method. This is apparent from the results of the change of the activity of producing L-glutamic acid throughout the cultivation by the present continuous culture method and the cell recycle culture method. The culture conditions shown in FIG. 1 is according to the method described in Unexamined Published Japanese Patent Application No. 62-48394. As to the present continuous culture method, however, 500 mg/l polyoxyethylene sorbitan monopalmitate was added, followed by continuous supply of a feeding solution containing glucose, $KH_2PO_4$, $MgSO_4$, soybean protein hydrolysate and polyoxyethylene sorbitan monopalmitate, and extraction of the culture broth. Thus, the method of the present invention can stably maintain the productivity of L-glutamic acid at a higher level than that by the cell recycle continuous culture.

Figure 2:
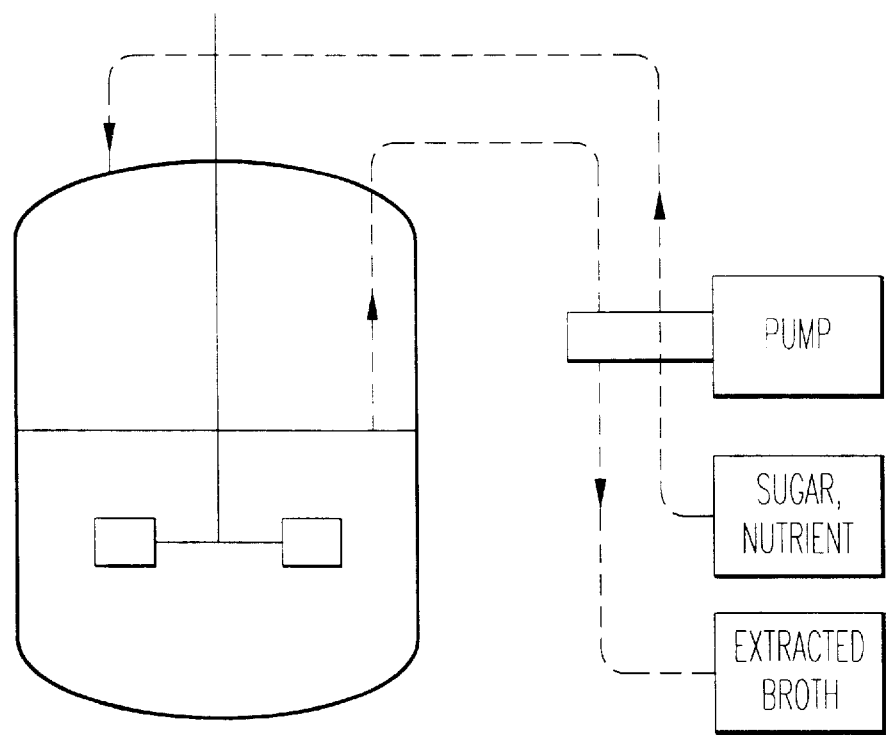
FIG. 2 shows one example of fermentor for use in the method of the present invention (single fermentor).

One representative example of the fermentation system to be used by the method of the present invention is shown in FIG. 2. Preferably, continuous culture procedures for producing L-glutamic acid while growing a fresh bacterium cell with the high productivity is generally carried out in a single fermentor from the respect of practical cultivation control. However, any continuous culture method to produce L-glutamic acid while growing bacteria may be satisfactory, irrespective of the number of the fermentors therefor. Several fermentors may sometimes be used, because the volume of a fermentor is small. In this case, fermentors are connected together linearly or in parallel for continuous culture, so that the high productivity of L-glutamic acid can be achieved provided that the culture conditions of each fermentor are conditions to produce L-glutamic acid under bacterial growth.

By the method of the present invention, L-glutamic acid can be produced continuously at a high production rate. Prolonged culture can be attained by using continuous production process, with the resulting reduction of laborious works. Furthermore, the system therefore is simple, compared with those by the cell recycle continuous culture method and the multi-step continuous culture method and the like, so that the present method is effective for reduction of fixed cost and bacterial contamination.

EXAMPLES

The present invention will be described in detail in the following examples.

Example 1

A medium (30 ml) containing 30 g/l glucose, 1 g/l $KH_2PO_4$, 0.4 g/l $MgSO_4·7 H_2O$, 4 g/l urea, 20 mg/l $FeSO_4·7 H_2O$, 20 mg/l $MnSO_4·4 H_2O$, 15 ml/l soybean protein hydrolysate, and 300 µg/l biotin was poured into a 500-ml flask, followed by sterilization under heating at 115° C. for 10 minutes. This was cooled to room temperature, followed by inoculation of Brevibacterium lactofermentum ATCC 13869 for seed culturing at 30° C. for 24 hours.

A medium (270 ml) containing 60 g/l glucose, 1 g/l $KH_2PO_4$, 1 g/l $MgSO_4$, 15 ml/l soybean protein hydrolysate, and 300 µg/l biotin was poured into a 1-liter fermentor preliminarily sterilized, followed by addition of the above-mentioned seed culture broth (30 ml), and the resulting culture was cultivated at 30° C. Aeration rate was 300 ml per minute, and the pH was kept at 7.5 with $NH_3$ gas.

Five hours after the initiation of the cultivation, polyoxyethylene sorbitan monopalmitate was added to a final concentration of 500 mg/l. To the fermentor, a feeding solution containing 180 g/l glucose, 1 g/l $KH_2PO_4$, 1 g/l $MgSO_4$, 15 ml/l soybean protein hydrolysate, and 500 mg/l polyoxyethylene sorbitan monopalmitate was continuously added at 30 ml per hour, and the same volume of the culture broth was extracted, to maintain the working volume in the reactor at a constant volume.

The sugar concentrations in all of the extracted culture broths were 5 g/l or less.

Figure 3:
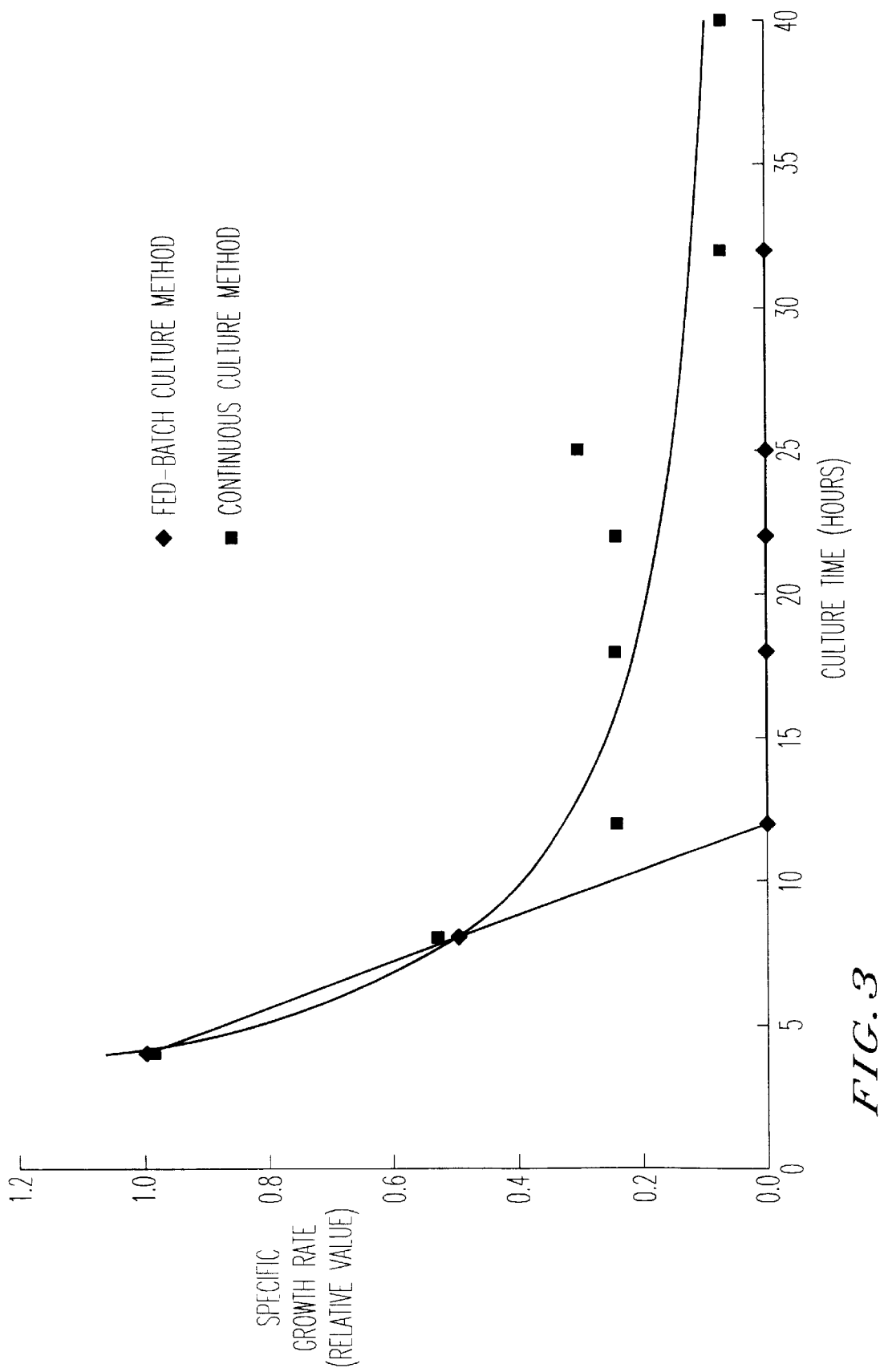
FIG. 3 shows change of specific growth rate over time, as observed in the continuous culture method of Example 1 and the comparative fed-batch culture method.

FIG. 3 shows the change of specific growth rate throughout the cultivation. Herein, the term "specific growth rate" means a proportional constant, provided that concentration dX of bacteria growing within very short time dT is in proportion to the concentration X of bacteria present at the time, which constant is represented in unit of liter/h (l/h). The concentration X is a dry weight of cells contained in a unit volume of the culture broth (expressed as "g/l"). Additionally, the relative value of the specific growth rate means a relative value when the specific growth rate at the initial stage of exponential growth is defined as 1. Unlike fed-batch culture method, bacterial growth is continued throughout the cultivation by the present continuous culture method.

The outcome of continuing the cultivation for 40 hours is such that the yield of L-glutamic acid was 56% and the productivity thereof was 5 g/l/hr. The yield was calculated by dividing the total amount of L-glutamic acid obtained in the cultivation by the total amount of sugar used in the cultivation, wherein the amounts are on weight basis. The productivity was calculated according to the formula mentioned herein before.

For comparison, a fed-batch culture method was also examined.

Specifically, a medium (270 ml) containing 60 g/l glucose, 1 g/l $KH_2PO_4$, 1 g/l $MgSO_4$, 15 ml/l soybean protein hydrolysate, and 300 µg/l biotin was poured into a 1-liter fermentor preliminarily sterilized, followed by addition of the above-mentioned seed culture broth (30 ml) for cultivation under the same conditions.

Five hours after the initiation of the cultivation, a greater amount of polyoxyethylene sorbitan monopalmitate was added to a final concentration of 2000 mg/l. At 6 ml/hour, a feeding solution containing 400 g/l glucose and 2000 mg/l polyoxyethylene sorbitan monostearate was continuously added. However, no extraction of the same volume of the culture broth was carried out, so that the working volume in the fermentor was increased. As shown in FIG. 3, under these conditions, the bacterial growth was terminated before 20 hours. Thus, the cultivation was continued up to the period of 40 hours, with the resulting outcome of 56% of yield of L-glutamic acid and 2.6 g/l/hr of productivity thereof. The yield was calculated in the same manner as the above. The productivity was calculated by dividing the amount of L-glutamic acid produced in the cultivation per unit volume of the final culture broth (g/l) by the culture time (hour).

Compared with the fed-batch culture method, the production of L-glutamic acid is 2-fold per unit time by the present continuous culture method, with significant improvement of the productivity.

Example 2

A medium (30 ml) containing 30 g/l glucose, 1 g/l $KH_2PO_4$, 0.4 g/l $MgSO_4·7 H_2O$, 4 g/l urea, 20 mg/l $FeSO_4·7 H_2O$, 20 mg/l $MnSO_4·4 H_2O$, 15 ml/l soybean protein hydrolysate, and 300 µg/l biotin was poured into a 500-ml flask, followed by sterilization under heating at 115° C. for 10 minutes. This was cooled to room temperature, followed by inoculation of Brevibacterium lactofermentum FERM BP-4172 (AJ 12821) for seed culturing at 30° C. for 24 hours.

A medium (270 ml) containing 60 g/l glucose, 1 g/l $KH_2PO_4$, 1 g/l MgSO4, 15 ml/l soybean protein hydrolysate, and 300 µg/l biotin was poured into a 1-liter fermentor preliminarily sterilized, followed by addition of the above-mentioned seed culture broth (30 ml), and the resulting culture was cultivated at 30° C. Aeration rate was 300 ml per minute, and the pH was kept at 7.5 with $NH_3$ gas. To the culture was added a feeding solution containing 300 g/l glucose, 1 g/l $KH_2PO_4$, 1 g/l $MgSO_4$, and 15 ml/l soybean protein hydrolysate continuously at 25 ml per hour, and the same volume of the culture broth was extracted, to maintain the working volume in the fermentor to a constant volume.

The sugar concentrations in all of the extracted culture broths were 5 g/l or less.

Figure 4:
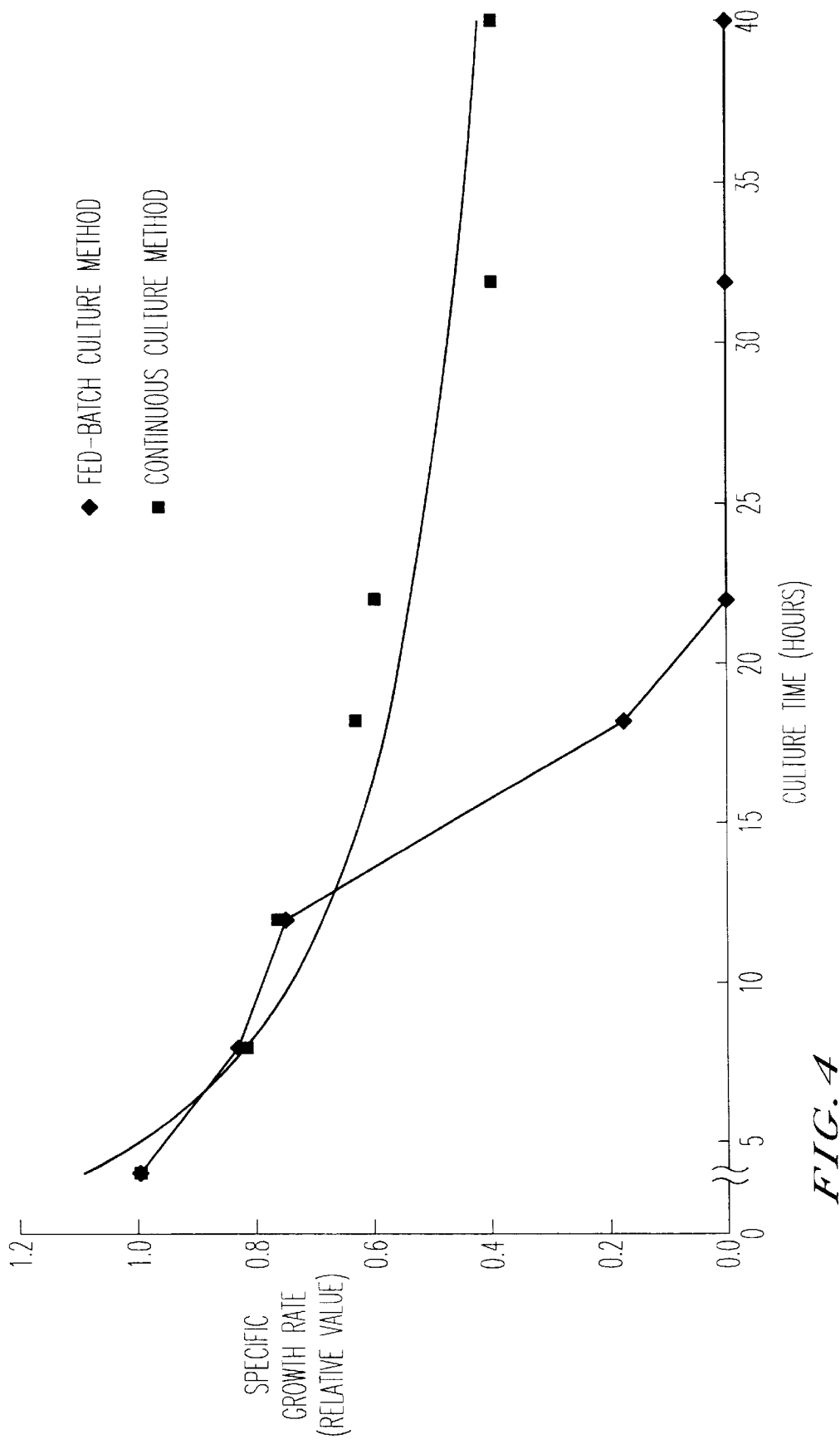
FIG. 4 shows change of specific growth rate throughout the cultivation, as observed in the continuous culture method of Example 2 and the comparative fed-batch culture method.

FIG. 4 shows the change of specific growth rate throughout the cultivation. It is indicated that bacterial growth is continued throughout the cultivation.

The outcome of continuing the cultivation for 40 hours is such that the yield of L-glutamic acid was 56% and the productivity thereof was 6.6 g/l/hr.

For comparison, a fed-batch culture method was also examined.

Specifically, a medium (270 ml) containing 60 g/l glucose, 1 g/l $KH_2PO_4$, 1 g/l $MgSO_4$, 15 ml/l soybean protein hydrolysate, and 300 µg/l biotin was poured into a 1-liter fermentor preliminarily sterilized, followed by addition of the above-mentioned seed culture broth (30 ml)

under the same conditions. At 7 ml/hour, a feeding solution containing 500 g/l glucose was continuously added into the culture, for up to 40 hours. The resulting outcome is 54% of yield of L-glutamic acid and 3.2 g/l/hr of productivity thereof.

The yields and the productivities were calculated in the same manner as in Example 1.

Compared with the fed-batch culture method, the production of L-glutamic acid is 2-fold per unit time by the present continuous culture method, with significant improvement of the productivity.

Example 3

A medium (30 ml) containing 30 g/l glucose, 1 g/l $KH_2PO_4$, 0.4 g/l $MgSO_4 \cdot 7 H_2O$, 4 g/l urea, 20 mg/l $FeSO_4 \cdot 7 H_2O$, 20 mg/l $MnSO_4 \cdot 4 H_2O$, 15 ml/l soybean protein hydrolysate, and 300 μg/l biotin was poured into a 500-ml flask, followed by sterilization under heating at 115° C. for 10 minutes. This was cooled to room temperature, followed by inoculation of *Brevibacterium lactofermentum* FERM BP-4172 (AJ 12821) for seed culturing at 30° C. for 24 hours.

A medium (270 ml) containing 60 g/l glucose, 1 g/l $KH_2PO_4$, 1 g/l $MgSO_4$, 15 mg/l soybean protein hydrolysate, and 300 μg/l biotin was poured into a 1-liter fermentor preliminarily sterilized, followed by addition of the above-mentioned seed culture broth, and the resulting culture was cultivated at 30° C. Aeration rate was 300 ml per minute, while the pH was kept at 7.5 with $NH_3$ gas. To the culture was added a feeding solution containing 180 g/l glucose, 1 g/l $KH_2PO_4$, 1 g/l $MgSO_4$, and 15 ml/l soybean protein hydrolysate continuously at 40 ml per hour, followed by extraction of the same volume of the culture broth, to maintain the working volume in the fermentor at a constant volume.

The sugar concentrations in all of the extracted culture broths were 5 g/l or less.

The outcome of continuing the cultivation for 100 hours is such that the yield of L-glutamic acid was 55% and the productivity thereof was 8.3 g/l/hr. The yield and the productivity were calculated in the same manner as in Example 1.

Figure 5:
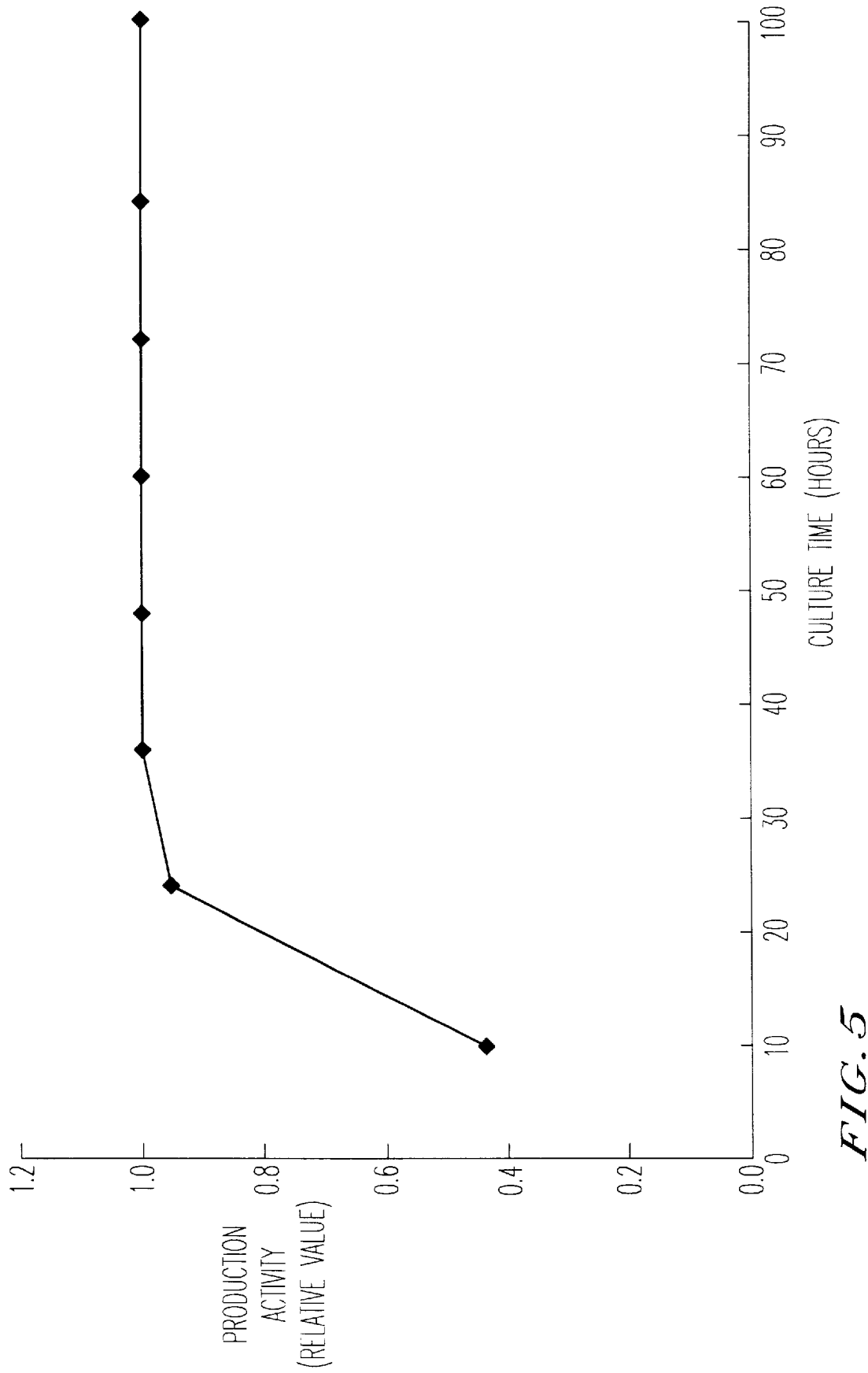
FIG. 5 shows change of activity of producing L-glutamic acid throughout the cultivation, as observed in the continuous culture method of Example 3.

FIG. 5 shows the change of the activity of producing L-glutamic acid throughout the cultivation. It is indicated that throughout the long time, the activity was maintained at a high level. The activity of producing L-glutamic acid was expressed as an amount of L-glutamic acid (g) produced in a unit time (hour) based on the weight of cells (dry weight: g).

What is claimed is:

1. A method for producing L-glutamic acid, comprising: inoculating a microorganism having an ability to produce L-glutamic acid into a liquid culture medium containing a carbon source and a nitrogen source, conducting continuous L-glutamic acid fermentation in which both a carbon source and a nutrient having an effect of promoting bacterial growth are added to the culture medium so as to cause the microorganism to grow, and then collecting L-glutamic acid produced and accumulated in the culture medium, wherein the microorganism is not removed from the culture medium and then recycled to the culture medium.

2. A method according to claim 1, wherein the microorganism having the ability to produce L-glutamic acid is a microorganism having a property to produce L-glutamic acid when the microorganism is cultured in a liquid culture medium at a biotin concentration of 10 μg/liter or more with no addition of any substance suppressing a biotin action.

3. A method according to claim 1, wherein the microorganism belongs to the genus Brevibacterium or Corynebacterium.

4. A method according to claim 1, wherein the microorganism has a reduced α-ketoglutarate dehydrogenase activity.

5. A method according to claim 1, wherein the carbon source comprises a sugar, an organic acid or an alcohol.

6. A method according to claim 1, wherein the nitrogen source comprises ammonia, ammonium salt, urea, nitrates or organic nitrogen sources.

7. A method according to claim 1, wherein the culture medium further contains inorganic salts.

8. A method according to claim 1, wherein the fermentation is conduced under aerobic conditions within a range of pH 5–6 and the temperature range of 25°–40° C.

9. A method according to claim 1, wherein the nutrient is a nitrogen salt, an organic salt or an organic micronutrient.

10. A method according to claim 9, wherein the organic micronutrient is an amino acid or a vitamin.

11. A method according to claim 1, wherein the fermentation is conducted in a single fermentor.

12. A method according to claim 1, wherein the fermentation is conducted in more than one fermentor.

* * * * *